United States Patent
Hanreich et al.

(10) Patent No.: US 9,902,976 B2
(45) Date of Patent: Feb. 27, 2018

(54) METHOD FOR IMPROVING SUBSTRATE DEGRADATION IN AGRICULTURAL BIOGAS PLANTS

(71) Applicant: Novozymes A/S, Bagsvaerd (DK)

(72) Inventors: Angelika Hanreich, Berlin (DE); Joachim Pheiffer, Wilnsdorf (DE); Joanna Wawrzynczyk, Bunkeflostrand (SE); Preben Nielsen, Hoersholm (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/120,617

(22) PCT Filed: Feb. 25, 2015

(86) PCT No.: PCT/EP2015/000589
§ 371 (c)(1),
(2) Date: Aug. 22, 2016

(87) PCT Pub. No.: WO2015/128095
PCT Pub. Date: Sep. 3, 2015

(65) Prior Publication Data
US 2017/0037435 A1    Feb. 9, 2017

(30) Foreign Application Priority Data

Feb. 25, 2014 (EP) .................... 14075010

(51) Int. Cl.
*C12N 9/24* (2006.01)
*C12P 5/02* (2006.01)

(52) U.S. Cl.
CPC ....... *C12P 5/023* (2013.01); *C12Y 304/21014* (2013.01); *C12P 2203/00* (2013.01); *Y02E 50/343* (2013.01)

(58) Field of Classification Search
CPC .................. C12P 5/023; C12N 9/24
See application file for complete search history.

(56) References Cited

FOREIGN PATENT DOCUMENTS

| DE | 4141832 C1 | | 5/1993 |
|---|---|---|---|
| DE | 102004042688 A1 | | 3/2006 |
| DE | 102015013859 | * | 5/2017 |
| WO | 2010/009400 A1 | | 1/2010 |
| WO | 2011/076123 A1 | | 6/2011 |
| WO | 2011/092136 A1 | | 8/2011 |
| WO | 2012/093041 A1 | | 7/2012 |
| WO | 2013083801 A2 | | 6/2013 |

OTHER PUBLICATIONS

Ahring, Advances in Biochemical Engineering/Biotechnology, vol. 81, pp. 1-220 (2003).
Ahring et al., Advances in Biochemical Engineering/Biotechnology, vol. 82, pp. 1-200 (2003).
Gerhardt et al., Presentation on "Enzymes for Biomass Pretreatment and Hydrolysis" given at European Biorefinerary Symposium in Flensburg (2008).
Gerhardt et al., Presentation on "Hydrolytische Enzyme zur Erhohung der Effizienz der Vergarung" given at Fachtagung Biogas 2008 Entwicklungen und Erfahrungen aus der Praxis in Potsdam (2008).
Mitsuiki et al., Enzyme and Microbial Technology, vol. 34, No. 5, pp. 482-489 (2004).

* cited by examiner

Primary Examiner — Maryam Monshipouri
(74) Attorney, Agent, or Firm — Eric J. Fechter

(57) ABSTRACT

The invention relates to the use of at least one bacterial amylase and/or bacterial or fungal cellulase in combination with one or more protease(s) in substrates for anaerobic digestion processes for biogas production for improving degradation of maize, maize silages and/or other biogas substrates, in particular for improving gas yield, velocity and substrate conversion rate.

20 Claims, 5 Drawing Sheets

SEQUENCE LISTING

<160> NUMBER OF SEQ ID NOS: 2

<210> SEQ ID NO 1
<211> LENGTH: 188
<212> TYPE: PRT
<213> ORGANISM: Nocardiopsis prasina
<220> FEATURE:
<221> NAME/KEY: MISC_FEATURE
<222> LOCATION: (1)..(188)
<223> OTHER INFORMATION: Serine protease family S1

<400> SEQUENCE: 1

Ala Asp Ile Ile Gly Gly Leu Ala Tyr Thr Met Gly Gly Arg Cys Ser
1               5                   10                  15

Val Gly Phe Ala Ala Thr Asn Ala Ala Gly Gln Pro Gly Phe Val Thr
            20                  25                  30

Ala Gly His Cys Gly Arg Val Gly Thr Gln Val Thr Ile Gly Asn Gly
        35                  40                  45

Arg Gly Val Phe Glu Gln Ser Val Phe Pro Gly Asn Asp Ala Ala Phe
    50                  55                  60

Val Arg Gly Thr Ser Asn Phe Thr Leu Thr Asn Leu Val Ser Arg Tyr
65                  70                  75                  80

Asn Thr Gly Gly Tyr Ala Thr Val Ala Gly His Asn Gln Ala Pro Ile
                85                  90                  95

Gly Ser Ser Val Cys Arg Ser Gly Ser Thr Thr Gly Trp His Cys Gly
            100                 105                 110

Thr Ile Gln Ala Arg Gly Gln Ser Val Ser Tyr Pro Glu Gly Thr Val
        115                 120                 125

Thr Asn Met Thr Arg Thr Thr Val Cys Ala Glu Pro Gly Asp Ser Gly
    130                 135                 140

Gly Ser Tyr Ile Ser Gly Thr Gln Ala Gln Gly Val Thr Ser Gly Gly
145                 150                 155                 160

Ser Gly Asn Cys Arg Thr Gly Gly Thr Thr Phe Tyr Gln Glu Val Thr
                165                 170                 175

Pro Met Val Asn Ser Trp Gly Val Arg Leu Arg Thr
            180                 185

<210> SEQ ID NO 2
<211> LENGTH: 269
<212> TYPE: PRT
<213> ORGANISM: Bacillus clausii
<220> FEATURE:
<221> NAME/KEY: MISC_FEATURE
<222> LOCATION: (1)..(269)
<223> OTHER INFORMATION: Serine Protease family S8A

<400> SEQUENCE: 2

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

-continued

```
Thr Gly Ile Ser Thr His Pro Asp Leu Asn Ile Arg Gly Gly Ala Ser
         35              40                  45

Phe Val Pro Gly Glu Pro Ser Thr Gln Asp Gly Asn Gly His Gly Thr
     50              55                  60

His Val Ala Gly Thr Ile Ala Ala Leu Asn Asn Ser Ile Gly Val Leu
 65              70                  75                      80

Gly Val Ala Pro Ser Ala Glu Leu Tyr Ala Val Lys Val Leu Gly Ala
             85              90                      95

Ser Gly Ser Gly Ser Val Ser Ser Ile Ala Gln Gly Leu Glu Trp Ala
             100             105                 110

Gly Asn Asn Gly Met His Val Ala Asn Leu Ser Leu Gly Ser Pro Ser
         115             120                 125

Pro Ser Ala Thr Leu Glu Gln Ala Val Asn Ser Ala Thr Ser Arg Gly
         130             135                 140

Val Leu Val Val Ala Ala Ser Gly Asn Ser Gly Ala Gly Ser Ile Ser
145             150             155                         160

Tyr Pro Ala Arg Tyr Ala Asn Ala Met Ala Val Gly Ala Thr Asp Gln
             165             170                 175

Asn Asn Asn Arg Ala Ser Phe Ser Gln Tyr Gly Ala Gly Leu Asp Ile
             180             185                 190

Val Ala Pro Gly Val Asn Val Gln Ser Thr Tyr Pro Gly Ser Thr Tyr
             195             200                 205

Ala Ser Leu Asn Gly Thr Ser Met Ala Thr Pro His Val Ala Gly Ala
         210             215                 220

Ala Ala Leu Val Lys Gln Lys Asn Pro Ser Trp Ser Asn Val Gln Ile
225             230                 235                     240

Arg Asn His Leu Lys Asn Thr Ala Thr Ser Leu Gly Ser Thr Asn Leu
             245                 250                 255

Tyr Gly Ser Gly Leu Val Asn Ala Glu Ala Ala Thr Arg
             260             265
```

METHOD FOR IMPROVING SUBSTRATE DEGRADATION IN AGRICULTURAL BIOGAS PLANTS

CROSS-REFERENCE TO RELATED APPLICATIONS

Figure 1:
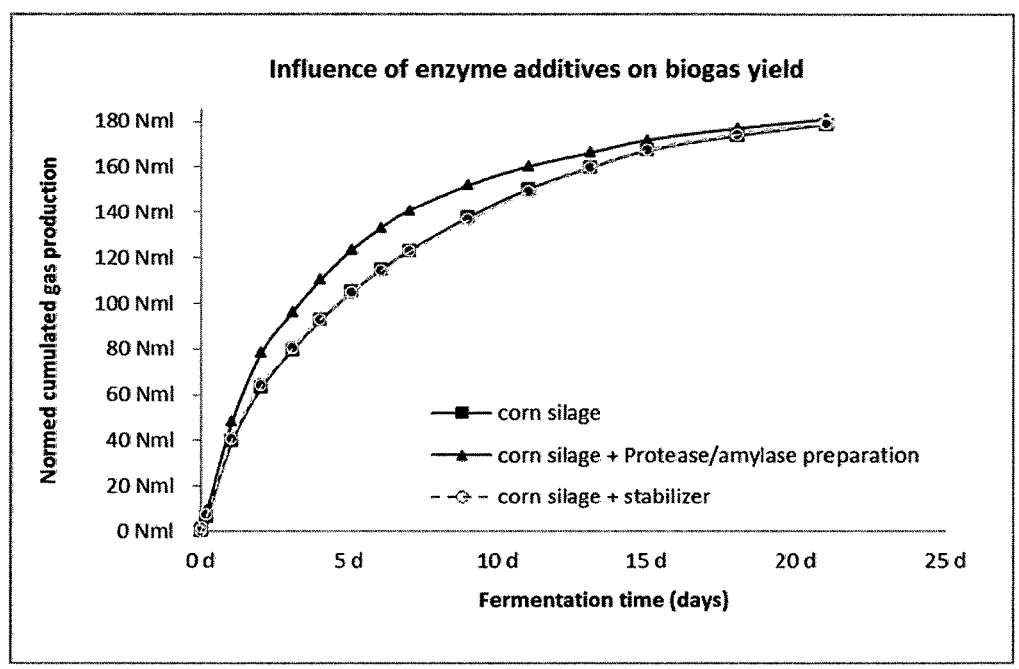

This application is a 35 U.S.C. 371 national application of PCT/EP2015/000589 filed Feb. 25, 2015, which claims priority or the benefit under 35 U.S.C. 119 of European application no. 14075010.0 filed Feb. 25, 2014. The content of these applications is fully incorporated herein by reference.

FIELD OF THE INVENTION

The invention concerns the production of biogas, which gains more and more in importance in economy. Biogas is produced by anaerobic microbiological degradation of liquid manure, energy plants (maize, grain), agricultural by-products or organic waste. It consists mainly of $CH_4$ and $CO_2$. $CH_4$ (share normally more than 50%) is used for the production of thermal and electrical energy. About 11% of the renewable energy is produced by the use of biogas in Germany (2009).

Modern biogas plants are equipped with industrial process measurement and control devices. Additives, such as trace element or enzyme preparations, are often used to optimize the biological process of anaerobic digestion. These additives can enhance metabolic action of the microorganisms or ameliorate substrate degradation. In the past, the application of carbohydrate-degrading enzyme preparations (carbohydrases) has been shown to be beneficial for the break-down of cellulose or hemicellulose in plant material to simple sugars. The resulting sugars are subsequently metabolized by acidogenic and acetogenic bacteria to acetic acid, $H_2$ and $CO_2$. These compounds are the substrates for methane production by methanogenic archea. Hence, beneficial effects on plant cell wall degradation are often reflected in increased biogas yields, reduced substrate input or reduced viscosity.

The invention is especially interesting for biogas plants, which are run entirely or to a large extent on renewable primary products, such as corn silage, grass silage or other whole plant silages. The utilization of recalcitrant substrates with high fiber contents, which is propagated for the production of second generation biofuels, makes the need for enzymatic additives more urgent. This is because the degradation of fiber-rich substrates is slow and incomplete. Furthermore, many biogas plants, which run on plant material alone, have C:N ratios outside the suggested range of 20 to 30.That is to say, the nitrogen content in many agricultural biogas plants is too low and, hence, the performance of microorganisms is suboptimal.

DESCRIPTION OF THE RELATED ART

There are several publications concerning the biogas production, see for instance the survey *Biomethanation I and II* (*Advances in Biochemical Engineering/Biotechnology*; volumes 81 and 82,Springer-Verlag Berlin Heidelberg GmbH, 2003). Many patents protect the production of biogas in biogas plants supported by enzymatic substrate degradation, some examples are given below.

In DE 4141832 (S. R. Dauber, priority date: 18 Dec. 1991) the novelty is a waste water treatment process and apparatus, which treats de-watered sludge. It consists of a mixture of activated sludge from a settlement tank and primary sludge. Further, it is described that the plant incorporates an anaerobically-operated acidification reactor, followed by an anaerobically-operated biogas reactor with the following features:
 (a) Protease, amylase, lipase, cellulase or mixtures thereof are introduced into the acidification reactor,
 (b) The acidification reactor is operated in the temperature range 20 to 70° C. in a pH range of 3.5 to 6.5.
 (c) The temperature and the pH value are set in the ranges as stated (b) above.

Later on, the German application DE102004042688 (Biopract GmbH, priority date Jan. 09, 2004) was published. It describes the acceleration of rotting and increasing gas production in waste water purification and biogas plants by adding mixed enzyme preparation to clarified sludge before entering gas-producing reactor. The enzyme preparation consists of one or more carboxyhydrases together with other hydrolyzing enzymes such as lipases and proteases.

In the years 2010/2011,some WO patent specifications of the Danish company Novozymes A/S were published.
 WO/2013/083801 (Title: Biogas from substrates comprising animal manure and enzymes) contains a biogas production process comprising the steps of providing a substrate comprising manure, and
  (a) adding one or more enzyme to the substrate, and then adding the substrate with the one or more enzyme to a biogas digester; or
  (b) adding the substrate to a digester tank and adding one or more enzyme to the tank. The enzymes are selected from amylolytic enzymes, lipolytic enzymes, proteolytic enzymes, cellulolytic enzymes, oxidoreductases and plant cell-wall degrading enzyme.
 WO 2012093041 A1 (Title: Process for producing biogas from pectin and lignocellulose containing material) relates to biogas production processes with enzymatic pre-treatment, said processes comprising the steps of providing a slurry comprising a lignocellulose- and pectin-containing material, water and two or more enzyme treatments; allowing the two or more enzyme-treatment steps to degrade the lignocellulose- and pectin-containing material, and adding the degraded material to a biogas digester tank at a suitable rate and ratio to effectively convert the material to biogas in the digester.
 WO 2011092136 (Title: Bio gas production process with enzymatic pre-treatment) contains a biogas production process with enzymatic pre-treatment; said process comprising the steps of providing a slurry comprising a lignocellulose-containing material, water and one or more enzyme; allowing the one or more enzyme to degrade the lignocellulose-containing material at a suitable temperature and pH; and adding the enzyme-degraded material to a biogas digester tank at a suitable rate and ratio to effectively convert the material to biogas in the digester.

OBJECTIVE OF THE INVENTION

The general objective of the invention is to enhance the yield of biogas in decomposition processes.

It is the goal of the present invention to provide a preferably improved alternative to the carbohydrase preparations, which are currently used in biogas plants. These products are supposed to improve degradation of plant material, to increase the gas yield or the speed of gas formation and/or to reduce viscosity in the fermenter.

SUMMARY OF INVENTION

It has now been found surprisingly that the combined use of an amylase and/or a NSP (Non-Starch-Polysaccharide)-degrading enzyme mixture with one or more proteolytic enzyme(s) results in the elevation of the total biogas yield and the speed of degradation of substrates, such as corn silage, grass silage, triticale silage and/or other whole-plant silages. Preferred proteases according to the invention are acid stable serine proteases derived from *Nocardiopsis dassonvillei* subsp. *dassonvillei* DSM 43235 (A1918L1), *Nocardiopsis prasina* DSM 15649, *Nocardiopsis prasina* (previously alba) DSM 14010, *Nocardiopsis* sp. DSM 16424, *Nocardiopsis alkaliphila* DSM 44657 and *Nocardiopsis lucentensis* DSM 44048, as well as homologous proteases.

These proteases are derived from *Nocardiopsis prasina* (previously alba) DSM 14010, *Nocardiopsis* sp. DSM 16424, *Nocardiopsis alkaliphila* DSM 44657 and *Nocardiopsis lucentensis* DSM 44048, as well as homologous proteases.

So far, there was no indication that the proteolytic capacity of the microbiota in biogas fermenters can be a limiting factor. If such an important activity was limited, this is an explanation of the observed synergistic effect of carbohydrases combined with one or more proteases.

Lately, it was found in lab experiments that the supplementation of carbohydrases with proteolytic enzymes further enhances the rate of biogas production. This is reflected either as an increase in in the total amount of biogas produced per kg substrate, or as a faster biogas production, e.g. measured as a higher biogas production during the first few days of the gassification. There are at least two possible explanations for this observation.

The first is that protein-carbohydrate complexes are cleaved, such as prolamin-starch complexes in maize kernels. This cleavage leads to the liberation of starch, which is otherwise shielded by prolamin, and can then be degraded by hydrolyzing bacteria. This leads to a higher amount of digestible carbohydrates and, subsequently, to a higher gas production.

The second explanation for the observed enzyme effect is that an enzymatic cleavage of proteins in the substrate results in peptides and amino acids. These compounds may be utilized by microorganisms as nitrogen source, which is crucial for the synthesis of all enzymes necessary in their metabolisms. A higher metabolic activity of the microbiota will then lead to a more efficient or faster biogas production.

In particular, the inventors of the present invention have found that the addition of a protease in combination with a carbohydrase, as for example an amylase or a NSP-degrading enzyme, results in a significant boost of the carbohydrase induced degradation and, hence, in the rate of gas production in the anaerobic biogas fermentation.

In a further embodiment, the invention relates to a method for improving the degradation of maize, maize silages and other whole-plant silages as substrate in anaerobic digesters by treating the substrate with an efficient amount of one or more proteolytic enzymes in combination with at least one carbohydrase.

DETAILED DESCRIPTION OF THE INVENTION

In the present context, a carbohydrase is an enzyme that catalyzes the breakdown of carbohydrates into simple sugars.

Examples of carbohydrases useful in the present context are glucanases, in particular beta-glucanases and xyloglucanases, cellulases, xylanases, amylases and pectinases and mixtures thereof. In a preferred embodiment of the invention, the carbohydrases are amylase and cellulase.

The carbohydrase for use according to the invention is stable in the presence of protease. The protease stability may be determined by incubating 0.5 mg purified carbohydrase enzyme protein/ml in a buffer at a desired pH (e.g. pH 3, 4, or 5), for the desired time (e.g. 30, 45, 60, 90, or 120 minutes) in the presence of protease (e.g. pepsin, 70 mg/l), and then raising pH to the desired pH (e.g. pH 4, 5, 6, 7, or 8) and measuring residual activity. The residual carbohydrase activity is preferably at least 20%, preferably at least 30, 40, 50, 60, 70, 80, or at least 90% relative to the control (a non-protease-treated sample).

In a particular embodiment at least one carbohydrase is an amylase, a cellulase or an enzyme mixture comprising at least one enzyme selected from the group consisting of beta-glucanases, xyloglucanases, xylanases, amylases and pectinases.

In the present context, an amylase is an enzyme that catalyzes the endo-hydrolysis of starch and other linear and branched oligo- and poly-alpha-1-4-D-glucosides. In a particular embodiment, the amylase for use according to the invention has alpha-amylase activity, which catalyzes the endohydrolysis of 1,4-alpha-glucosidic linkages in oligosaccharides and polysaccharides. Alpha-amylases act, e.g., on starch, glycogen and related polysaccharides and oligosaccharides in a random manner, liberating reducing groups in the alpha-configuration.

In a preferred embodiment the amylase of the invention is an alpha-amylase (systematical name: 1,4-alpha-D-glucan glucanohydrolase), preferably a bacterial amylase. In further embodiments, the amylase of the invention belongs to the EC 3.2.1.-group of amylases, such as EC 3.2.1.1 (alpha-amylase), EC 3.2.1.2 (beta-amylase), EC 3.2.1.3 (glucan 1,4-alpha-glucosidase, amyloglucosidase, or glucoamylase), EC 3.2.1.20 (alpha-glucosidase), EC 3.2.1.60 (glucan 1,4-alpha-maltotetraohydrolase), EC 3.2.1.68 (isoamylase), EC 3.2.1.98 (glucan 1,4-alpha-maltohexosidase), or EC 3.2.1.133 (glucan 1,4-alpha-maltohydrolase).

In a preferred embodiment, the amylase for use according to the invention can be, or is, classified as belonging to the EC 3.2.1.1 group. The EC numbers refer to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web at www.chem.qmw.ac.uk/iubmb/enzyme/index.html.

Amylase activity may be determined by any suitable assay. Generally, assay-pH and assay-temperature may be adapted to the enzyme in question. Examples of assay-pH-values are pH 2, 3, 4, 5, 6, 7, 8,9, 10, 11, or 12. Examples of assay-temperatures are 30, 35, 37, 40, 45, 50, 55, 60, 65, 70, 80, 90, or 95° C. Preferred pH values and temperatures are in the physiological range, such as pH values of 3, 4, 5, 6, 7, or 8, and temperatures of 30, 35, 37, or 40° C. The following amylase assay can be used: Substrate: Phadebas tablets (Pharmacia Diagnostics; cross-linked, insoluble, blue-coloured starch polymer, which is mixed with bovine serum albumin and a buffer substance, and manufactured into tablets). Assay Temperature: 37° C. Assay pH: 4.3 (or 7.0, if desired). Reaction time: 20 min. After suspension in water the starch is hydrolyzed by the alpha-amylase, giving soluble blue fragments. The absorbance of the resulting blue solution, measured at 620 nm, is a function of the alpha-amylase activity. One Fungal alpha-Amylase Unit (1 FAU) is the amount of enzyme which breaks down 5.26 g starch per hour at the standard assay conditions. A preferred starch is Merck, Amylum solubile Erg. B. 6, Batch 9947275. For a taxonomical classification and identification of bacteria reference is made to Bergey's Manual of Systematic Bacteriology (1986), vol 2, ISBNO-683-0783. In the alternative, the well-known 16SrRNA sequence analysis can be used (see e.g. Johansen et al, Int. J. Syst. Bacteriol, 1999, 49, 1231-1240, in particular the Methods section on p. 1233, $2^{nd}$ column); or taxonomy experts can be consulted, e.g. from DSMZ or other recognized depositary institutes. As employed herein the term bacterial designates amylases that are derived from bacteria. The term "derived from" includes enzymes obtainable, or obtained, from wild type bacterial strains, as well as variants thereof. The variants may have at least one substitution, insertion, and/or deletion of at least one amino acid residue in comparison with the parent enzyme from which it is derived. The term variant also includes shufflants, hybrids, chimeric enzymes and consensus enzymes. The variants may have been produced by any method known in the art, such as site-directed mutagenesis, random mutagenesis, consensus derivation processes (EP 897985), and gene shuffling (WO 95/22625, WO 96/00343), etc. For the present purposes an amylase variant qualifies as bacterial when at least one bacterial amylase has been used for its design, derivation or preparation. The term bacterial does not refer to a potential recombinant production host but only to the origin of the amylase encoding gene that is hosted by it. The amylase for use according to the invention is preferably derived from a strain of *Bacillus*, such as strains of *Bacillus amyloliquefaciens, Bacillus circulans, Bacillus halmapalus, Bacillus licheniformis, Bacillus megaterium, Bacillus* sp., *Bacillus stearothermophilus*, and *Bacillus subtilis;* preferably from strains of *Bacillus amyloliquefaciens, Bacillus halmapalus, Bacillus licheniformis, Bacillus* sp., *Bacillus subtilis,* and *Bacillus stearothermophilus.*

Non-limiting examples of wildtype amylases for use according to the invention are those derived from *Bacillus licheniformis*, such as Swissprot entry name AMY_BACLI, primary accession number P06278; *Bacillus amyloliquefaciens*, such as Swissprot entry name AMY_BACAM, primary accession number P00692; *Bacillus megaterium*, such as Swissprot entry name AMY_BACME, primary accession number P20845; *Bacillus circulans*, such as Swissprot entry name AMY_BACCI, primary accession number P08137; *Bacillus stearothermophilus*, such as Swissprot entry name AMY_BACST, primary accession number P06279. Another example is from *Bacillus subtilis*, such as Swissprot entry name AMY_BACSU, primary accession number P00691.

For purposes of the present invention, preferred amylases are the amylases contained in the following commercial products: BAN, Stainzyme, Termamyl SC, Natalase, and Duramyl (all from Novozymes), and in the Validase BAA and Validase HT products (from Valley Research). Further particular examples of amylases for use according to the invention are the amylases contained in the following commercial products: Clarase, DexLo, GC 262 SP, G-Zyme G990, G-Zyme G995, G-Zyme G997, G-Zyme G998, HTAA, Optimax 7525, Purastar OxAm, Purastar ST, Spezyme AA, Spezyme Alpha, Spezyme BBA, Spezyme Delta AA, Spezyme DBA, Spezyme Ethyl, Spezyme Fred (GC521), Spezyme HPA, and Ultraphlow (all from Genencor); Validase HT340L, Valley Thin 340L (all from Valley Research); Avizyme 1500, Dextro 300 L, Kleistase, Maltazyme, Maxamyl, Thermozyme, Thermatex, Starzyme HT 120 L, Starzyme Super Conc, and Ultraphlo.

In a particular embodiment, the amylase for use according to the invention is pelleting stable, and/or thermostable. The melting temperature (Tm) of an enzyme is a measure of its thermostability. The amylase of the invention may have a Tm of at least 75° C., 76° C., 77° C., 78° C., 79° C., 80° C., 81° C., 82° C., 83° C., 84° C., 85° C., 86° C., 87° C., 88° C., 89° C., 90° C., 92° C., 93° C., 94° C. or at least 95° C., as determined by Differential Scanning 91° C., Calorimetry (DSC). The DSC is performed in a 10 mM sodium phosphate, 50 mM sodium chloride buffer, pH 7.0. The scan rate is constant, e.g. 1.5° C./min. The interval scanned may be from 20 to 100° C. Another buffer may be selected for the scanning, e.g. a buffer of pH 5.0, 5.5, 6.0, or pH 6.5. In further alternative embodiments, a higher or lower scan rate may be used, e.g. a lower one of 1.4° C./min, 1.3° C./min, 1.2° C./min, 1.1° C./min, 1.0° C./min, or 0.9° C./min.

In another preferred embodiment, the amylase for use according to the invention has an activity at pH 7.0 and 37° C. of at least 35% relative to the activity at the pH-optimum and 37° C. More preferably, the activity at pH 7.0 and 37° C. is at least 40, 45, 50, 55, 60, 65, 70, or at least 75% of the activity at the pH-optimum and 37° C.

In another preferred embodiment, the amylase of the invention has an activity at pH 7.0 and 37° C. and in the presence of 5mM bile salts of at least 25% relative to the activity at the pH-optimum and 37° C. in the absence of bile salts. More preferably, the activity at pH 7.0 and 37° C. and in the presence of 5mM bile salts is at least 30, 35, 40, 45, 50, 55, 60, or at least 65% of the activity at the pH-optimum and 37° C. in the absence of bile salts.

A commercially available bacterial amylase for use according to the present invention is RumiStar® (DSM Nutritional Products AG).

Other relevant carbohydrases are NSP-hydrolysing enzymes, such as glucanases, in particular beta-glucanases and xyloglucanases, cellulases, xylanases and pectinases.

In the present context, a cellulase is an enzyme that catalyzes the hydrolysis of cellulose. In a preferred embodiment the cellulase of the invention is (systematical name: 4-β-D-glucan 4-glucanohydrolase) preferably a fungal cellulase. In further embodiments, the celluase of the invention belongs to the EC 3.2.1.-group glycosidases, i.e. enzymes hydrolysing O- and S-glycosyl compounds, such as EC 3.2.1.4 (cellulase), EC 3.2.1.6, EC 3.2.1.14, EC 3.2.1.21, EC 3.2.1.73, EC 3.2.1.74, EC 3.2.1.91, EC 3.2.1.151, EC 3.2.1.165, EC 3.2.1.176. In a particular embodiment, cellulase catalyzes the endohydrolysis of (1→4)-β-D-glucosidic linkages in cellulose and other oligosaccharides and polysaccharides. Cellulases act, e.g., on cellulose and related polysaccharides and oligosaccharides in a random manner, liberating reducing groups in the alpha-configuration.

The EC numbers refer to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web at www.chem.qmw.ac.uk/iubmb/enzyme/index.html.

Commercially available fungal cellulase preparations for use according the present invention are MethaPlus®, Axiase™ (DSM), ZyMaxx and JBS.

In the present context, a beta-glucanase is an enzyme that catalyzes the endohydrolysis of linkages in beta-D-glucans (E.C.3.2.1.4, E.C.3.2.1.6, E.C.3.2.1.39, E.C.3.2.1.58, E.C.3.2.1.71, E.C.3.2.1.73, E.C.3.2.1.74, E.C.3.2.1.75, E.C.3.2.1.91, E.C.3.2.1.151, E.C.3.2.1.155 and E.C.3.2.1.176). Substrates include laminarin, lichenin, cereal D-glucans and others.

In the present context, a xyloglucanase is an enzyme that catalyzes reaction involves endohydrolysis of 1,4-beta-D-glucosidic linkages in xyloglucan with retention of the beta-configuration of the glycosyl residues (E.C.3.2.1.151)

In the present context, a xylanase is an enzyme that catalyzes the xylosidic linkage in xylans. This enzymatic activity can be found in the enzyme classes E.C.3.2.1.8, E.C.3.2.1.32, E.C.3.2.1.136 and E.C.3.2.1.156.

In the present context, a pectinase is an enzyme that catalyzes the random hydrolysis of (1→4)-alpha-D-galactosiduronic linkages in pectate and other galacturonans (E.C.3.2.1.15)

The EC numbers refer to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web at www.chem.qmw.ac.uk/iubmb/enzyme/index.html.

Proteases, or peptidases, catabolize peptide bonds in proteins breaking them down into fragments of amino acid chains, or peptides.

Proteases are classified on the basis of their catalytic mechanism into the following groups: serine proteases, EC 3.4.21.-, (S), cysteine proteases (C), aspartic proteases (A), metalloproteases (M), and unknown, or as yet unclassified, proteases (U), see Handbook of Proteolytic Enzymes, A. J. Barrett, N. D. Rawlings, J. F. Woessner (eds), Academic Press (1998), in particular the general introduction part.

Proteases for use according to the invention are acid stable proteases.

In a particular embodiment, the protease for use according to the invention is a microbial protease, the term microbial indicating that the protease is derived from, or originates from a microorganism, or is an analogue, a fragment, a variant, a mutant, or a synthetic protease derived from a microorganism. It may be produced or expressed in the original wild-type microbial strain, in another microbial strain, or in a plant; i. e. the term covers the expression of wild-type, naturally occurring proteases, as well as expression in any host of recombinant, genetically engineered or synthetic proteases. Examples of microorganisms are bacteria, e. g. bacteria of the phylum Actinobacteria phy. nov., e. g. of class I: Actinobacteria, e. g. of the Subclass V: Actinobacteridae, e. g. of the Order I: Actinomycetales, e. g. of the Suborder XII: Streptosporangineae, e. g. of the Family II: Nocardiopsaceae, e. g. of the Genus I: *Nocardiopsis*, e. g. Nocardiopsis sp. NRRL 18262, and *Nocardiopsis alba*; e.g. of the species *Bacillus* or mutants or variants thereof exhibiting protease activity. This taxonomy is on the basis of Berge's Manual of Systematic Bacteriology, 2nd edition, 2000, Springer (preprint: Road Map to Bergey's).

The term serine protease refers to serine peptidases and their clans as defined in the above Handbook. In the 1998 version of this handbook, serine peptidases and their clans are dealt with in chapters 1-175. Serine proteases may be defined as peptidases in which the catalytic mechanism depends upon the hydroxyl group of a serine residue acting as the nucleophile that attacks the peptide bond. Examples of serine proteases for use according to the invention are proteases of Clan SA, e. g. Family S2 (Streptogrisin), e. g. Sub-family S2A (alpha-lytic protease), as defined in the above Handbook.

Protease activity can be measured using any assay, in which a substrate is employed, that includes peptide bonds relevant for the specificity of the protease in question. There are no limitations on the origin of the acid stable serine protease for use according to the invention. Thus, the term protease includes not only natural or wild-type proteases, but also any mutants, variants, fragments etc. thereof exhibiting protease activity, as well as synthetic proteases, such as shuffled proteases, and consensus proteases. Such genetically engineered proteases can be prepared as is generally known in the art, e. g. by Site-directed Mutagenesis, by PCR (using a PCR fragment containing the desired mutation as one of the primers in the PCR reactions), or by Random Mutagenesis. The preparation of consensus proteins is described in e. g. EP 0 897 985.

Examples of acid-stable proteases for use according to the invention are proteases derived from *Nocardiopsis* sp. NRRL 18262, and *Nocardiopsis alba* and proteases of at least 60, 65, 70, 75, 80, 85, 90, or at least 95% amino acid identity to any of these proteases.

For calculating percentage identity, any computer program known in the art can be used. Examples of such computer programs are the Clustal V algorithm (Higgins, D. G., and Sharp, P. M. (1989), Gene (Amsterdam), 73, 237-244

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et aL, 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

$$(\text{Identical Residues} \times 100)/(\text{Length of Alignment} - \text{Total Number of Gaps in Alignment})$$

In another particular embodiment, the protease for use according to the invention, besides being acid-stable, is also thermostable.

The term thermostable means for proteases one or more of the following: That the temperature optimum is at least 50° C., 52° C., 54° C., 56° C., 58° C., 60° C., 62° C., 64° C., 66° C., 68° C., or at least 70° C.

A commercially available serine proteases derived from *Nocardiopsis* is Ronozyme®ProAct® (DSM Nutritional Products AG).

In a particular embodiment, the amylase and the protease, in the form in which they are added to the substrate, or when being included in a substrate additive, are well-defined.

Well-defined means, that the enzyme preparation is at least 50% pure on a protein-basis. In other particular embodiments the enzyme preparation is at least 60, 70, 80, 85, 88, 90, 92, 94, or at least 95% pure. Purity may be determined by any method known in the art, e.g. by SDS-PAGE, or by Size-exclusion chromatography (see Example 12 of WO 01/58275).

A well-defined enzyme preparation is advantageous. For instance, it is much easier to dose correctly to the substrate an enzyme that is essentially free from interfering or contaminating other enzymes. The term dose correctly refers in particular to the objective of obtaining consistent and constant results, and the capability of optimising dosage based upon the desired effect.

Enzyme preparations with purities of this order of magnitude are in particular obtainable using recombinant methods of production, whereas they are not so easily obtained and also subject to a much higher batch-to-batch variation when produced by traditional fermentation methods.

In the use according to the invention, the enzyme combinations described above can be added to the biogas fermenter before, after, or simultaneously with the substrate. The latter is preferred. This applies to both, liquid and solid formulations. The dosage has to be adapted to the respective biogas fermenter.

In one preferred embodiment at least one carbohydrase is added to the digester and the at least one carbohydrase is added in amounts coresponding to 0.1-500 mg enzyme protein/kg substrate; preferably 0.2-250 mg enzyme protein/kg substrate, preferably 0.2-100 mg enzyme protein/kg substrate, preferably 0.2-50 mg enzyme protein/kg substrate, preferably 0.2-10 mg enzyme protein/kg substrate, preferably 0.5-5 mg enzyme protein/kg substrate.

In another preferred embodiment the one or more proteolytic enzymes each ar added in amounts corresponding to 0.1-500 mg enzyme protein/kg substrate, preferably 0.2-250 mg enzyme protein/kg substrate, preferably 0.2-100 mg enzyme protein/kg substrate, preferably 0.2-50 mg enzyme protein/kg substrate, preferably 0.2-10 mg enzyme protein/kg substrate, preferably 0.5-5 mg enzyme protein/kg substrate.

The application of enzyme preparations, which contain proteolytic and carbohydrolytic enzyme activities, was shown to boost biogas production by more than 10%. Possible reasons for this significant enhancing effect and some advantages of using enzyme additives with the described, combined lead activities in biogas plants over the supplementation with commercially available products are as follows:

First, the addition of carbohydrase-protease preparations catalyzes the cleaving of protein-carbohydrate complexes (e.g. prolamin-starch complexes in maize kernels), which results in the liberation of simple sugars as a carbon source and peptides as a nitrogen source. The incorporation of short peptides or amino acids during the microbial protein synthesis is more favorable than the synthesis of proteins from other nitrogen compounds, such as $NH_4^+$. Raising the nitrogen availability is expected to lead to higher metabolic activities of the microbiota. This should generally lead to higher biogas yields. Also, because enzymes are catalysts, they are generally not consumed in the reaction they catalyze. Therefore, it is expected that their actions last for a longer period of time without a significant nitrogen accumulation in the digestate.

The present invention is further described by the following examples which should not be construed as limiting the scope of the invention.

EXAMPLES

Chemicals used as buffers and substrates were commercial products of at least reagent grade.

Example 1

Modified Batch Test Based on VDI 4630

Target:

The aim of the investigations is to determine the cumulative normalized gas volume produced from a chosen substrate by an anaerobic microbial culture. Gas produced is determined via the measurement of gas pressure due to accumulating gas volume in the head space of the fermentation vessel. Fermentation conditions are described as a so called headspace test.

Method:

The test is a 15 ml batch fermentation carried out in 50 ml vessels in the following manner:

In two independent experiments, 4 replicates of the batches are cultivated over 21 days at 39° C. At start time ($t_o$) each fermentation bottle, except the controls, contains 15 ml of a described anaerobic culture, a substrate and an additive. Controls do not contain the is active, enzymatic additive. They may contain inactive additives, such as the stabilizing matrix of the respective enzyme preparation or no additive at all. Gas pressure in the head space, which is the result of gas formation during fermentation, is measured once per day in the first week, every second day in the second week and every third day in the last week. Normalized gas formation is calculated and compared to corresponding controls.

Fermentations are carried out in so-called headspace bottles (Rollrandflaschen) ND20, 50 ml, No. 1 400 118 LA, Burdich Laborbedarf GmbH & Co. KG with 20 mm aluminum caps with septum No. 1 400 711. It is necessary, to measure the bottle volume very accurately. Then it is possible to calculate head space volume very exact. Vessel volume is measured via mass determination with distilled water. Weight has to be determined exactly down to four significant digits after the decimal point. The experimental procedure is as follows: For every single experimental variant four vessels (labelled, exact volume known) including caps and septa have to be prepared. The weight of each individual flask including cap and septum is measured. The exact substrate amount is transferred to the bottles according to the experimental design (usually 80 to 200 mg oDM). The preparation of inoculum depends on the source and on the experimental design. As inoculum, an anaerobic culture according VDI 4630, from industrial biogas plants, sludge from waste water treatment plants or own lab fermentation processes with dry matter contents of less than 4% and organic dry matter contents of 50-80% (of DM) can be used.

The necessary amount of inoculum is collected and stored in a Woulfs bottle at 39° C. For the set-up of the batch experiment, fermentation vessels are filled with 15 ml inoculum and all additives of fixed volumes. Dosage of the inoculum is made with a Watson-Marlow-dosage pump 520 DIU350. During manipulation, i.e. harvest and dosage, the inoculum is floated with collected biogas from other fermentations. Before closing the vessels, they are flushed with $N_2$ for 20 seconds. Then they are capped and closed with a special device (Fa. CS-Chromatographie GmbH, Langerwehe). All bottles are mixed vigorously in order to suspend insoluble substrates. The total weight of each bottle is determined.

Fermentation is started by transferring the flasks to a 39° C. water bath. Gas pressure in the headspace of each replicate is measured after one hour. These values represent start pressure of fermentation and all further gas values are cumulated to this first value. Gas pressure measurement is carried out with a Digital Manometer Kobold HND-P236.

For gas pressure measurements, a needle (0.45×25 mm, 26 G×1", Fa. B. Braun, Melsungen AG), which is connected to the manometer via Luer lock, is pierced through the septum. The gas pressure of each replicate is stored and data is transferred to a computer for analysis. After measuring and data storage, the gas of all vessels is released by introducing a needle into the septum of the vessel. After 5 hours of incubation, the second pressure measurement is carried. Then, the gas pressure is measured once a day, always at the same time to ensure 24 h intervals. Every day, at least one hour before starting measurements, vessels are shaken. The interval of gas measurements may be stretched to two or more days, if the pressure increase per day is lower than 100 mbar.

Output of these tests are (a) gas formation curves over normally 21 days (mean values), (b) gas formation velocity (Nml gas per day or per hour), (c) relative gas formation (compared to corresponding control), (d) statistical analysis including MV; SD; confidence interval and if necessary T-Test of two groups of values, (e) gas yields (value accepted until daily gas production is lower than 1% of cumulated gas)

Example 2

Anaerobic Degradation of Maize and Other Whole-Plant Silages Using Enzyme Additives, which have Proteolytic and Carbohydrolytic Activities (FIG. 1)

In the described experiment, the general set-up of the modified batch test described in Example 1 was applied. Dried and milled corn silage, triticale silage and grass silage were used as single substrates for biogas production. The batch fermentations were inoculated with a microbial, biogas producing community taken from a laboratory fermenter and incubated at 39° C. for three weeks. The pH of the samples was measured in the beginning of the experiment after sample set-up (pH=7.3) and in the end of the experiment after three weeks of incubation (pH=7.1).

In order to test the effect of combined amylase and protease activities, samples were incubated with an enzyme preparation containing a *Nocardiopsis*-derived protease (Ronozyme ProAct) and amylase (Ronozyme RumiStar). The controls lacked the enzyme itself. In order to exclude an influence by the stabilizing matrix of the enzyme preparation, this stabilizing matrix alone was added to the controls. The concentration of the enzyme preparation and of the stabilizer used in this experiment was 20,000 ppm (20 mg enzyme per g dry substrate).

On all tested substrates, a significant increase of the biogas production was observed. For corn silage (FIG. 1), the gas yield was increased by roughly 20% compared to the control during the first 10 days of fermentation. The gas yield from triticale whole-grain-silage was increased by up to 15% and the gas yield from grass silage by roughly 20% during the first 7 days of fermentation. The culture, which was nitrogen-limited, produced biogas at a significantly faster rate from all substrates, if the enzyme preparation was added.

Example 3

Figure 2:
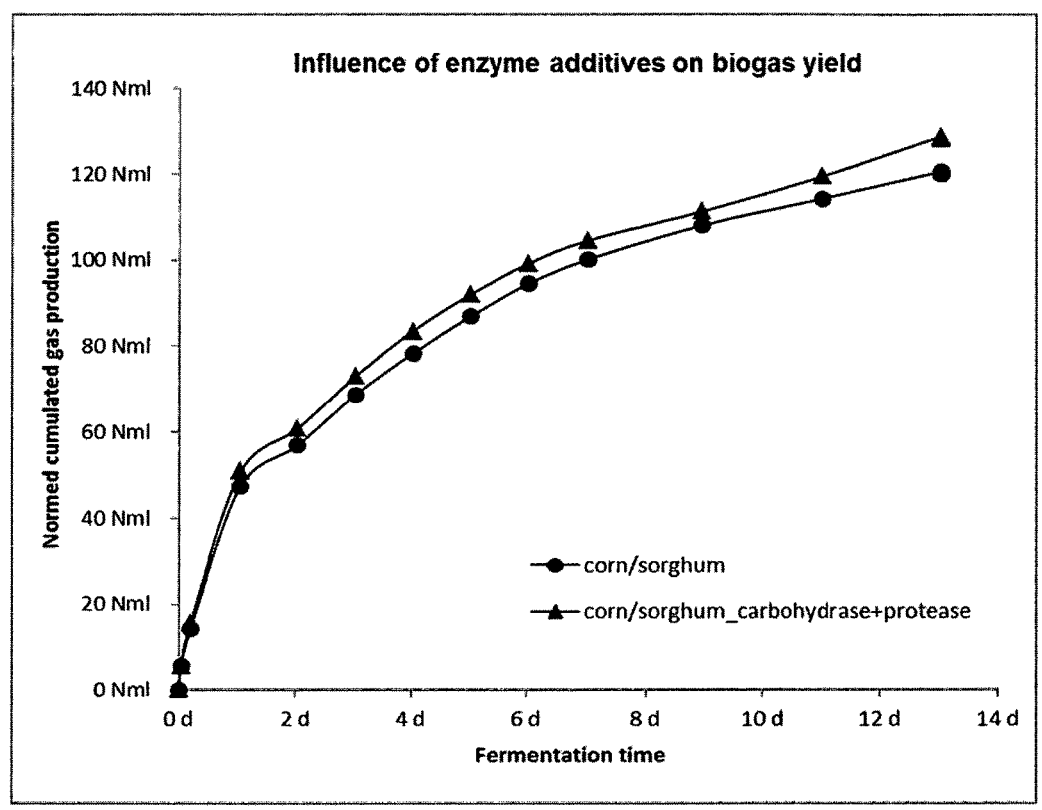

Anaerobic Degradation of Maize Silage and Sorghum using Enzyme Additives, which have Proteolytic and Carbohydrolytic Activities (FIG. 2)

In the described experiment, the general set-up of the modified batch test described in Example 1 was applied. Dried and milled corn silage and sorghum silage (50/50% w/w) were used as substrate for biogas production. The batch fermentations were inoculated with a microbial, biogas producing community taken from an industrial fermenter. All samples were incubated at 39° C. for three weeks. The pH of the samples was measured in the beginning of the experiment after sample set-up (pH=6.7) and in the end of the experiment after three weeks of incubation (pH=6.9).

In order to test the effect of combined cellulase and protease activities, samples were incubated with an enzyme preparation containing a *Nocardiopsis*-derived protease (Ronozyme ProAct) and a commercial cellulase preparation (Zymaxx). The concentration of the enzyme preparation used in this experiment was 20,000 ppm (20 mg enzyme per g dry substrate).

Combined cellulase-protease preparations led to an increase of the biogas production. The increase of the gas yield observed ranged between 6-8%.

The reason for this observation could be that the microbial consortium was not only energy-limited (carbon source), but also limited in nitrogen. Only if both limitations are addressed, more biogas is produced. Hence, the combined application of preparations with protease and carbohydrase activities shows effects superior to the application of is enzyme preparations featuring only one of these lead activities.

Example 4

Figure 3:
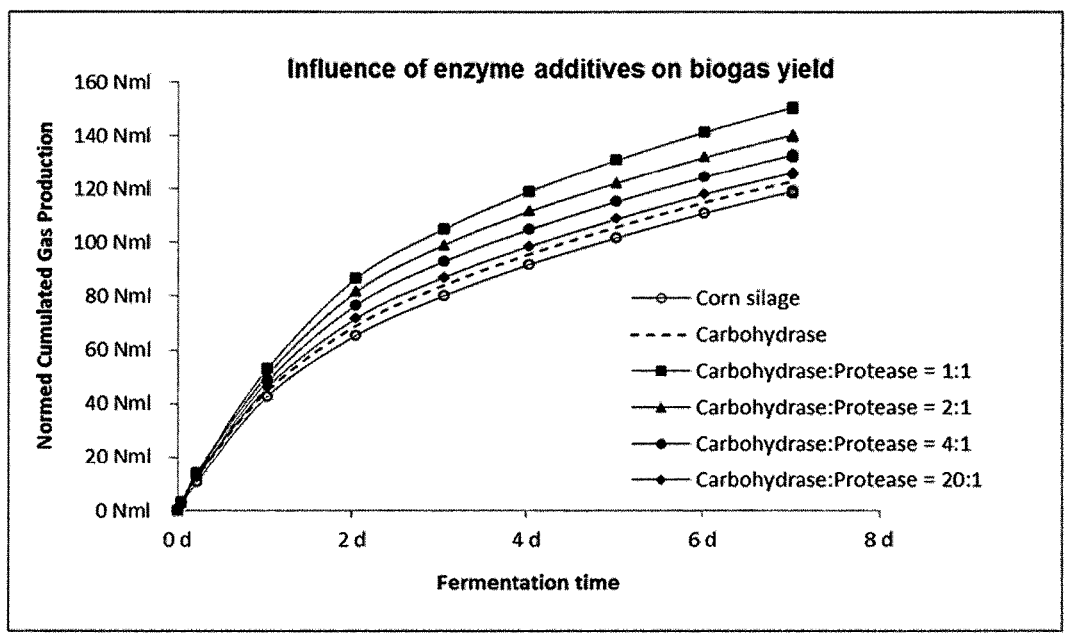

Anaerobic Degradation of Maize Silage using Enzyme Preparations, which Contain Different Carbohydrase to Protease Ratios (FIG. 3)

In the described experiment, the general set-up of the modified batch test described in Example 1 was applied. Dried and milled corn silage was used as substrate for biogas production. The batch fermentations were inoculated with a microbial, biogas producing community taken from an laboratory fermenter. All samples were incubated at 39° C. for three weeks. The pH of the samples was measured in the beginning of the experiment after sample set-up (pH=7.5) and in the end of the experiment after three weeks of incubation (pH=7.1).

In order to test the effect of combined amylase and protease activities, samples were incubated with an enzyme preparation containing a *Nocardiopsis*-derived protease (Ronozyme ProAct) and a commercial amylase preparation (MATS L). The concentration of the enzyme preparation used in this experiment was 20,000 ppm (20 mg enzyme per g dry substrate).

The beneficial effect of the combined administration of a carbohydrase and a protease was observed over a wide range of dosages. Experiments showed that enzyme mixtures composed of a amylase and a protease in ratios of 20:1 (20,000 ppm amylase and 1,000 ppm protease) to 1:1 (20,000 ppm amylase and 20,000 ppm protease) had significant effects on the biogas production. The increase of biogas after one week of incubation was 5% for the carbohydrase alone. Preparation with the combined lead activities yielded increases of 38% (c:p=1:1), 26% (c:p=2:1), 17% (c:p=4:1) and 8% (c:p=20:1).

Example 5

Comparison of the Effect on Biogas Yield Caused by Different Protease Additives

In the described experiment, the modified batch test described in Example 1 was performed in order to show the superior effect of the serine protease from *Nocardiopsis* compared to other protease preparations.

Dried and milled corn silage was used as substrate for biogas production. The batch fermentations were inoculated with a microbial, biogas producing community taken from a laboratory fermenter. All samples were incubated at 39° C. for three weeks. The pH of the samples was measured in the beginning of the experiment after sample set-up (pH=7.3) and in the end of the experiment after three weeks of incubation (pH=7.1).

Three different, commercial protease preparations, which contained protein in equal concentrations, were added to the substrate in equal amounts (20,000 ppm=20 mg enzyme per g dry substrate). No carbohydrase containing preparation was added. Therefore, observed effects could be clearly attributed to one enzyme class only.

Figure 4:
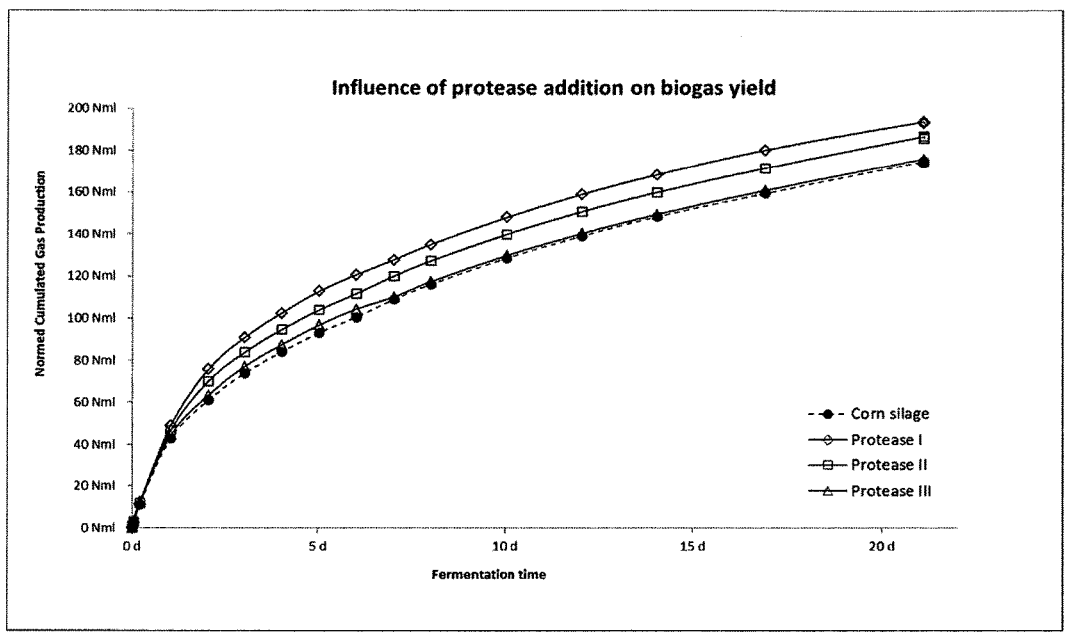

It was shown that two of the protease preparations led to an increased biogas yield (FIG. 4). Protease I led to the highest increase of the biogas yield (20% compared to the control). The effect of protease II was lower (12%) but still significant. Protease III had no significant effect on the biogas production. All tested proteases were serine proteases. Protease I and II were of bacterial origin whereas protease III was of fungal origin (Tab. 1).

It can be concluded that the degradation of proteins to peptides or amino acids can stimulate a microbial community and, subsequently, increase the biogas yield.

Surprisingly, the protease I derived from *Nocardiopsis* sp. (Ronozyme ProAct) had the strongest impact on biogas production and is, hence, superior to other members of this enzyme family.

TABLE 1

Increase of biogas yields caused by different proteases

| Product | Protein concentration (mg protein per g preparation) | Origin of the enzyme | Increase of biogas yield after | | | Significance |
|---|---|---|---|---|---|---|
| | | | 2 days | 7 days | 21 days | |
| Protease I | 75 | *Nocardiopsis* | 31% | 26% | 20% | + |
| Protease II | 88 | *Bacillus* | 19% | 15% | 12% | + |
| Protease III | 75 | *Aspergillus* | 5% | 2% | 1% | − |

Example 6

Figure 5:
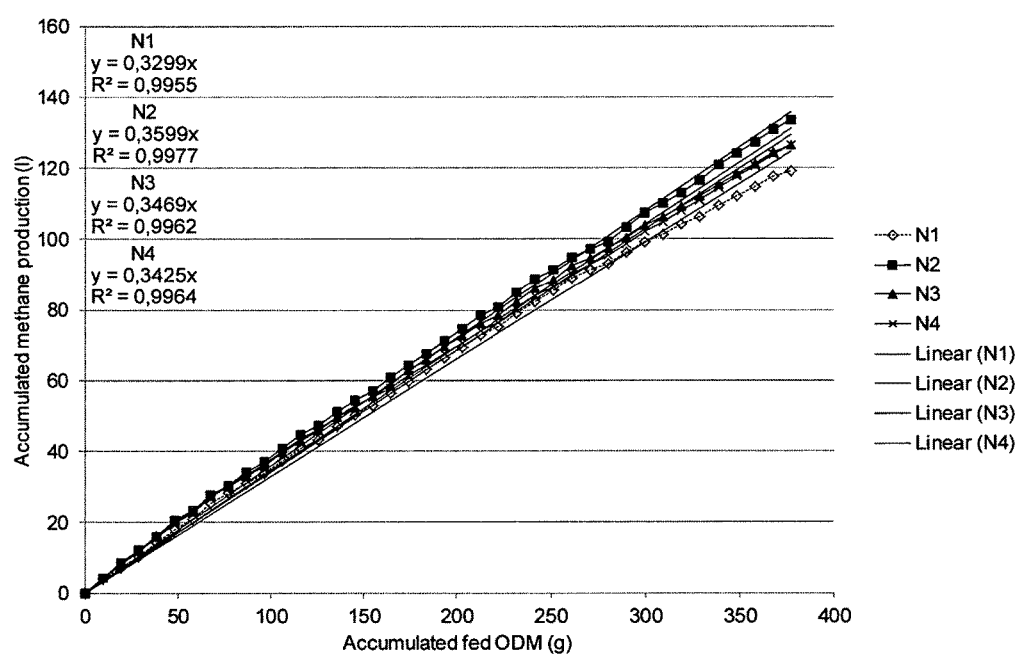

Anaerobic Digestion of Maize Silage in Presence of Protease—Semi-Continuously Operated Test (FIG. 5)

The aim of the experiment was to evaluate the effect of proteolytic enzyme addition on the continuous anaerobic digestion of maize silage. The effect of one serine protease (originated from *Nocardiopsis prasina*) with different dosing strategies was studied. For the experiment, four laboratory scale continuously stirred reactors with an active volume is of four liters, were used. The reactors were equipped with a top mounted propeller for mixing and a gas measuring device (AnoxKaldnes, Sweden). Methane content of produced biogas has been analyzed daily. Substrate, fresh maize silage, feeding was done manually once a day during the week, no feeding was done during the weekend. The working temperature of the reactors was 37° C. The inoculum used in the experiment was taken from the laboratory digester fed with maize silage with trace elements addition. As a result of the known deficiency of trace elements during mono-fermentation of maize silage, trace elements (AnoxKaldnes, Sweden) were added once a week during the experimental period. The retention time (HRT) was 60 days during the experiment with a loading of 2.5 kg DM/(m$^3$·d) which gives 2.4 kg ODM/(m$^3$·d). The experiment was carried out for 107 days. The, Dry Matter, DM-content in the substrate was diluted to 15%. Enzyme addition started on day 15, after steady state conditions in all four reactors were reached. The enzyme used in the experiment was serine protease of family S1 from *Nocardiopsis prasina* (see section 2.6.8. Seq ID NO 1), with the following dosing procedure (Table 2): Reactor N1—no enzyme added—Reference, Reactor N2—1% of DM in reactor, enzyme dosing once a week, Reactor N3—1% of incoming substrate DM, enzyme dosing every day, Reactor N4—5% of incoming substrate DM, enzyme dosing every day.

The methane yield in the four reactors can be seen in FIG. 5, where the accumulated methane production and the accumulated fed organic dry matter (ODM) are plotted. The slope of the linear regression is equal to the mean yield over the examined period (Table 2). Reactor 2 produced in average 9% more methane than the reference reactor (Reactor 1), while reactor 3 and 4 produced 5 and 3% more respectively. Earlier experience with the used reactors has shown on a 5% margin of error on gas production. These results therefore indicate that the enzyme addition has had a positive effect on the gas production in Reactor 2.

The dry matter (DM) content in the reactors was stable during the experiment period and no difference could be seen between the reactors. The DM reduction was approximately 79% in all reactors when taking into account a volume reduction per week & reactor. The pH started at 7.3, decreased to 7.1 but then seemed to stabilize around 7.2. The VFA-levels have been constantly low during the experiment. This indicates that the hydrolysis is the rate limiting step and the following steps in the degradation process have enough time to take care of the metabolites. The ammonium concentrations (NH$_4$-N) varied between 300-700 mg/l during the experiment. Comparing the mean values gives an increase in ammonium concentration of 27, 18 and 24% respectively in Reactor 2, 3 and 4. Higher levels of NH4-N show that more protein has been degraded and it seems in this case as the protease dosing once per week (with 1% of incoming DM during the week) has as high effect as the dosing every day with 5% per incoming DM. The COD-concentrations decreased from 7000 mg/l to 4000-5000 mg/l in the later part of the experiment. No difference could be seen between the reactors.

TABLE 2

Enzyme addition to the four CSTR and methane yield

| Reactor | Enzyme dose | Enzyme addition (daily or weekly) | Methane yield (Nm$^3$/ton ODM) |
|---|---|---|---|
| N1 | Reference | — | 330 |
| N2 | 10 g/kg digester DM | Once a week | 360 |
| N3 | 10 g/kg DM substrate fed | Once a day | 347 |
| N4 | 50 g/kg DM substrate fed | Once a day | 343 |

Example 7

Improved Production Rate of Biomethane by Addition of Proteolytic Enzyme to Manure Biogas Process The aim of this study was to show that the production rate of methane increases when additional microbial protease is added to the biogas process. The proteases investigated were a serine protease of family S1 from *Nocardiopsis prasina* (Seq ID NO 1, Protease 1) and a serine protease of family S8A from *Bacillus clausii* (Seq ID NO 2, two batches of protease 2, protease 2A and protease 2B were tested). The study was made on a biogas digestate containing pig manure added various undefined industrial waste primarily waste from food production. The study was made under laboratory conditions as biogas batch experiment, by determination of methane production. Methane was measured by Gas chromatography.

Protocol for Biogas Batch Experiments
  Equipment/Materials
  500 ml infusion bottles (Apodan Nordic)
  Bromine-butyl Stoppers for infusion bottles (Apodan Nordic 050974)
  N2 (AGA art no)
  Syringe, 50 ml (BD Plastipak 300865)
  Needle for 50 mL syringe (BD Microlance 304432)
  Syringe, 1 ml disposable polycarbonate (BD Plastipak 300013)
  Needle for 1 mL syringe (BD Microlance 300300)
  Valve, Mininert syringe valve for luer tip syringe (Mikrolab art PS-654051)
  Needle (needle from disposable 1 ml syringe) (BD medical)
  Methane standard from 30%, 60% and 100% methane (30 and 60%, diluted with N2)
  (Mikrolab, Arhus, Denmark ML42571)
  Vent/chamber for Biogas standards with septum (ML72052)
  Supelco, Precleaned 2 cm$^3$ Clear Screw Cap Vials (art 27339) (Supelco, Bellafonte, Pa., USA) (lids was tightend manually to ensure they were properly closed.

Biogas Digestate

The biogase digestate used as inoculum in this experiment was obtained from a commercial Biogas plant Snertinge Biogas (Snertinge, Denmark) 20 L manure from the anaerobic digester was tapped in 25 L plastic jerry can. The inoculum was sieved through 2 mm sieve, the filtrate was used for the experiments.

Bottle Experiment

In 500 ml infusion bottles the enzymes (Protease 1 or Protease 2) were added in a 500 µl dilution, in order to have identical final volumes in all flasks (to keep headspace volume similar). Enzymes were tested at two concentrations either 1.6 mg or 0.4 mg enzyme per bottle. For each concentration a negative control was included. For the negative control same amount of enzyme was added, the enzyme in the negative control was inactivated by autoclaving for 20 min at 121° C. Bottles were added 200 ml of biogas digestate. The bottle was flushed with $N_2$ for 30-60 s to remove $O_2$ from headspace. Bottles were closed with Stoppers for infusion bottles. Bottles were shaking by turning upside down at least 4 times to mix enzyme with biogas digestate. Bottles were incubated at 52° C. During the experiment bottles were shaken 2-3 times/week (as described above) Samples for Bio-methane determination were collected after 7, 14, 21 and 28 days. In order to correct for the vented volume, samples for GC are prepared immediately before and after venting. After 6 days bottles were vented in order to avoid to high pressure. Venting was performed with 50 mL syringe, the needle was pierced through stopper of the 500 ml bottle. 50 ml gas was removed (If pressure in the bottle did not allow 50 ml to be removed the bottle was not vented. If there was very high pressure in the bottle more than 50 ml was removed.

Preparation of Samples from Batch Bottles

For determination of Bio-methane, duplicate samples were prepared except for day 6 where one sample was taken before and after venting of the bottles. Samples were taken with a 1 mL syringe with valve between needle and syringe, by; Piercing needle through stopper of the 500 ml batch bottle with the valve open. The syringe was flushed 2-3 times in the bottle. 250 µl of gas was collected in the syringe. Valve was closed. The needle was pierced through stopper of 2 ml GC vial. Valve was opened. The 250 µl gas was injected into the 2 ml GC vial.

Preparation of Standards (Standard Curve)

The standards were prepared using the same type of syringe as for samples. The valve of the standard was opened until pressure is established in the chamber (septum has to be changed frequently). The needle was pierced through septum of the standard with the valve open. The syringe was flushed 2-3 times in the chamber. At least 250 µl of gas was taken into the syringe. The needle was removed from the septum with the valve open. Volume was adjusted to 250 µl, by pressing out excessive gas. The gas was injected into a 2 mL GC vial. Standard curve was made by measuring two independent vials prepared as described above containing 30, 60 or 100% methane.

Gas Chromatography Method for Determination of Bio-Methane Content in Biogas
  Equipment
  Varian 3900 GC with CP 8400 autosampler and FID detector, PoraPLOT Q (10 µm) 25 m×0.32 mm fused silica (Cat No. 7551)
  Equipment Settings
  Autosampler settings, autosampler is equipped with 10 µl Hamilton syringe,
  Autosampler "enabled", sample penetration depth "90%", solvent penetration depth "90%"
  Default Wash, Vial "I", volume "5.0 µl", Strokes "1", Draw up speed "5.0 µl/s".
  Clean Mode, Pre-Injection Solvent Flushes "3", Pre-Injection Sample Flushes "0", Post-Injection Solvent Flushes "1", Clean Solvent Source "I".
  Column Pneumatics, "Isobaric", Pressure "7.20 Psi".
  Detactor, Heater "ON" Setpoint "250° C.",
  Adjustments Electronics "YES", Time Constant "FAST"
  FID Event Table, Time; Initial, Range;12, Autozero; Yes.
  Detector EFC: Type 11, Helium Flow (Makeup) "25 ml/min", H2 Flow "30 ml/min",
  Method The samples were tested in a method where the column temperature was kept constant at 40° C., the methane peak occurred at about 1 min, and was integrated, and the area was used for the calculation. µmol $CH_4$ in standard was calculated for the three standards, and the slope of the standard curve was used for calculation of ml $CH_4$. Bio-methane amount in the samples using the formula:

$$\mu mol\ CH_4\ in\ standard = \frac{p \times 250 \times \%\ CH_4}{T_{actual} \times 0.0821}$$

$$mL\ CH_4 = \frac{Vol_{headspace} \times T \times 0.0821 \times Average_{(area1, area2)}}{Vol_{sample} \times Slope_{std}}$$

Definitions in the formula: mL $CH_4$ is mL Bio-methane, $VOl_{headspace}$ is volume of is headspace in bottle in mL, VOI$_{sample}$ in mL, T is temperature in Kelvin, which is 273, because with want to determine mL bio methane at 0° C., Average$_{(area1, area2)}$ is average of the area of the methane peak in the two GC determinations, Slope$_{std}$ is slope of the methane standard curve. P is the actual room temperature in K when standards curve was made, %CH4 is the concentration of the respective standard.

Results and Conclusion

Table 3 showing all data from Biogas Batch trials %CV is calculated from triple determinations.

Table 4 showing increase in bio methane production relative to a sample added same amount of enzyme inactivated by heat treatment.

Both proteolytic enzymes (Protease 1 is a protease belonging to the S1A family, Protease 2 (Savinase) belongs to S8A family in the MEROPS classification system) cause increased bio-methane production at more than 10% in the first 3 days after addition. The conclusion is that addition of protease to the biogas process leads to a faster release of protease.

Sequence Lists

Serine protease family S1 from *Nocardiopsis prasina*
Seq ID NO 1
ADIIGGLAYTMGGRCSVGFAATNAAGQPGFVTAGHCGRVGTQVTIGNGRG
VFEQSVFPGNDAAFVRGTSNFTLTNLVSRYNTGGYATVAGHNQAPIGSSV
CRSGSTTGWHCGTIQARGQSVSYPEGTVTNMTRTTVCAEPGDSGGSYISG
TQAQGVTSGGSGNCRTGGTTFYQEVTPMVNSWGVRLRT Serine protease family S8A from *Bacillus clausii*
Seq ID NO 2
AQSVPWGISRVQAPAAHNRGLTGSGVKVAVLDTGISTHPDLNIRGGASFV
PGEPSTQDGNGHGTHVAGTIAALNNSIGVLGVAPSAELYAVKVLGASGSG
SVSSIAQGLEWAGNNGMHVANLSLGSPSPSATLEQAVNSATSRGVLVVAA
SGNSGAGSISYPARYANAMAVGATDQNNNRASFSQYGAGLDIVAPGVNVQ
STYPGSTYASLNGTSMATPHVAGAAALVKQKNPSWSNVQIRNHLKNTATS
LGSTNLYGSGLVNAEAATR

TABLE 3

|  |  |  | day 0 |  | day 1 |  | day 2 |  | day 3 |  | day 6 |  | day 9 |  | day 14 |  | day 27 |  |
|---|---|---|---|---|---|---|---|---|---|---|---|---|---|---|---|---|---|---|
|  |  |  | ml CH4 | % CV | ml CH4 | % CV | ml CH4 | % CV | ml CH4 | % CV | ml CH4 | % CV | ml CH4 | % CV | ml CH4 | % CV | ml CH4 | % CV |
| Inoculum |  |  | 3 | 22% | 109 | 7% | 157 | 5% | 183 | 4% | 246 | 5% | 283 | 3% | 330 | 3% | 364 | 7% |
| Protease 1 | 0.01 | 0 | 3 | 8% | 129 | 5% | 192 | 3% | 217 | 2% | 268 | 2% | 296 | 2% | 330 | 4% | 348 | 5% |
| Protease 1 | 0.01 | Neg | 2 | 6% | 120 | 1% | 162 | 2% | 192 | 2% | 261 | 1% | 299 | 1% | 341 | 2% | 396 | 7% |
| Protease 1 | 0.0025 | 0 | 2 | 31% | 128 | 9% | 183 | 5% | 210 | 5% | 269 | 5% | 309 | 5% | 352 | 3% | 405 | 2% |
| Protease 1 | 0.0025 | Neg | 2 | 6% | 114 | 3% | 167 | 2% | 194 | 1% | 261 | 1% | 306 | 1% | 354 | 2% | 427 | 3% |
| Protease 1 | 0.01 | 0 | 3 | 17% | 135 | 4% | 180 | 2% | 202 | 4% | 260 | 3% | 299 | 2% | 343 | 2% | 387 | 4% |
| Protease 2A | 0.01 | Neg | 4 | 19% | 104 | 11% | 143 | 8% | 165 | 8% | 221 | 9% | 257 | 9% | 297 | 8% | 338 | 8% |
| Protease 2A | 0.0025 | 0 | 2 | 73% | 125 | 1% | 166 | 1% | 188 | 2% | 250 | 2% | 286 | 1% | 328 | 1% | 362 | 3% |
| Protease 2A | 0.0025 | Neg | 3 | 12% | 106 | 8% | 152 | 8% | 182 | 8% | 245 | 9% | 288 | 9% | 332 | 9% | 381 | 9% |
| Protease 2A | 0.01 | 0 | 3 | 3% | 140 | 5% | 195 | 6% | 221 | 3% | 282 | 3% | 320 | 3% | 367 | 4% | 405 | 3% |
| Protease 2B | 0.01 | Neg | 2 | 25% | 121 | 5% | 170 | 8% | 192 | 7% | 254 | 8% | 295 | 7% | 339 | 6% | 389 | 4% |
| Protease 2B | 0.0025 | 0 | 3 | 12% | 125 | 4% | 168 | 5% | 194 | 6% | 253 | 6% | 294 | 5% | 336 | 4% | 364 | 8% |
| Protease 2B | 0.0025 | Neg | 3 | 7% | 114 | 4% | 160 | 2% | 185 | 3% | 245 | 3% | 286 | 2% | 324 | 1% | 357 | 3% |

TABLE 4

|  | mg enzyme/ bottle | Increased Bio-methane relative to control added inactive enzyme |  |  |  |  |  |  |
|---|---|---|---|---|---|---|---|---|
|  |  | 1 | 2 | 3 | 6 | 9 | 14 | 27 |
| Protease 1 | 1.6 | 7% | 16% | 12% | 3% | −1% | −3% | −14% |
| Protease 1 | 0.4 | 11% | 9% | 7% | 3% | 1% | −1% | −5% |
| Protease 2A | 1.6 | 23% | 20% | 19% | 15% | 14% | 13% | 13% |
| Protease 2A | 0.4 | 15% | 9% | 4% | 2% | −1% | −1% | −5% |
| Protease 2B | 1.6 | 14% | 13% | 13% | 10% | 8% | 8% | 4% |
| Protease 2B | 0.4 | 9% | 4% | 4% | 3% | 3% | 4% | 2% |

LEGEND OF THE FIGURES

FIG. 1: Degradation of corn silage in batch fermentations.

The observed effect is attributed to the enzyme preparation only. A partial effect of the enzymes' stabilizing agent can be excluded as the negative control, for which enzyme stabilizer was used, did not influence the gas yield.

FIG. 2: Degradation of corn and sorghum silage in batch fermentations.

The influence of the combined carbohydrase and protease preparation on the degradation of a recalcitrant substrate is shown.

FIG. 3: Degradation of corn silage in batch fermentation. The influence of the preparation with combined lead activities is shown. In order to illustrate the positive effects, carbohydrase:protease ratios ranging from 1:1 to 20:1 were tested.

FIG. 4: Increase of biogas yields caused by different proteases

It was shown that two of the protease preparations led to an increased biogas yield.

FIG. 5: The methane yield in the four reactors can be seen.

Accumulated methane production as a function of accumulated fed ODM, where the slope of the linear regression gives the methane yield. N1 is reference reactor, N2—1% protease added weekly based on total DM in the reactor, N3—1% protease added daily based on DM of substrate fed to a reactor, N4—5% protease added daily based on DM of substrate fed to a reactor.

The invention claimed is:

1. A method for treating a substrate for biogas production in an anaerobic digester, which comprises treating the substrate with an efficient amount of a protease, wherein the protease has at least 85% amino acid identity to SEQ ID NO: 1 or to SEQ ID NO: 2.

2. The method of claim 1, wherein the protease is an S1 serine protease.

3. The method of claim 2, wherein S1 serine protease is a *Nocardiopsis* S1 serine protease.

4. The method of claim 3, wherein the S1 serine protease is a *Nocardiopsis alkaliphile, Nocardiopsis dassonvillei, Nocardiopsis lucentensis*, or *Nocardiopsis prasina* S1 serine protease.

5. The method of claim 4, wherein the S1 serine protease is obtained from *Nocardiopsis alkaliphila* DSM 44657, *Nocardiopsis dassonvillei* subsp. *dassonvillei* DSM 43235, *Nocardiopsis lucentensis* DSM 44048, *Nocardiopsis prasina* DSM 15649, *Nocardiopsis prasina* DSM 14010, or *Nocardiopsis* sp. DSM 16424.

6. The method of claim 1, wherein the protease has at least 90% amino acid identity to SEQ ID NO: 1 or to SEQ ID NO: 2.

7. The method of claim 1, wherein the protease has at least 95% amino acid identity to SEQ ID NO: 1 or to SEQ ID NO: 2.

8. The method of claim 1, wherein the protease has the amino acid sequence of SEQ ID NO: 1 or SEQ ID NO: 2.

9. The method of claim 1, wherein the protease is thermostable.

10. The method of claim 1, wherein the protease is acid stable.

11. The method of claim 1, wherein the substrate is a plant material.

12. The method of claim 11, wherein the plant material is selected from the group consisting of maize, maize silage, corn silage, grass silage, triticale silage and other whole plant silage.

13. The method of claim 1, wherein the substrate comprises liquid manure, agricultural byproducts or organic waste.

14. The method of claim 1, further comprising treating the substrate with a carbohydrase.

15. The method of claim 14, wherein the carbohydrase is selected from the group consisting of amylases, cellulases, beta-glucanases, pectinases, xylanases, xyloglucanases, and combinations thereof.

16. The method of claim 14, wherein the carbohydrase is added in an amount of 0.1-500 mg enzyme protein/kg substrate.

17. The method of claim 1, wherein the protease is added in an amount of 0.1-500 mg enzyme protein/kg substrate.

18. The method of claim 1, wherein the treatment is at a temperature above 20° C. and below 70° C.

19. The method of claim 1, wherein the treatment is at a pH above 4.5 and below 9.0.

20. A method for producing biogas in an anaerobic digester, wherein the substrate is treated using a method of claim 1.

* * * * *